United States Patent

Naka et al.

[11] Patent Number: 5,183,899
[45] Date of Patent: Feb. 2, 1993

[54] PYRAZOLE DERIVATIVE

[75] Inventors: Takehiko Naka, Kobe; Kohei Nishikawa, Kyoto, both of Japan

[73] Assignee: Takeda Chemical Industries, Ltd., Osaka, Japan

[21] Appl. No.: 560,759

[22] Filed: Jul. 31, 1990

[30] Foreign Application Priority Data

Aug. 2, 1989 [JP] Japan ................................. 1-200963
Sep. 11, 1989 [JP] Japan ................................. 1-235124
Nov. 10, 1989 [JP] Japan ................................. 1-293459

[51] Int. Cl.⁵ .................. C07D 403/10; A61K 31/415
[52] U.S. Cl. .................................................. 548/253
[58] Field of Search ......................... 548/253; 514/381

[56] References Cited

U.S. PATENT DOCUMENTS 4,880,804 11/1989 Carini et al. ...................... 514/234.5
5,015,651 5/1991 Carini et al. ......................... 548/252

FOREIGN PATENT DOCUMENTS 0028833 5/1981 European Pat. Off. .
0028834 5/1981 European Pat. Off. .
0245637 11/1987 European Pat. Off. .
0253310 1/1988 European Pat. Off. .
0291969 11/1988 European Pat. Off. .
0323841 7/1989 European Pat. Off. .

OTHER PUBLICATIONS

Bolis et al., J. Med. Chem, 30, 1729-1737, 1987.
Denkewalter et al., Progress in Drug Research, vol. 10, 510-512, (1966).
Haber et al., J. Cardiovascular Pharmacology, 10 (Supp. 7), 554-58, (1987).
Plattner et al., J. Med. Chem., 31, 2277-2288, (1988).
Burger, A., Medicinal Chemistry, Interscience Publishers, Inc., New York, pp. 565-571, 578-581, 600-601 (1960).

Primary Examiner—Mary C. Lee
Assistant Examiner—Lenora Ava Miltenberger
Attorney, Agent, or Firm—Wegner, Cantor, Mueller & Player

[57] ABSTRACT

Novel pyrazole derivatives of the formula (I):

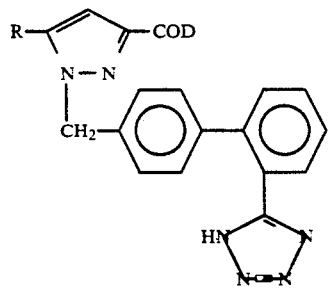

wherein R is an alkyl group and D is an alkoxy group, a hydroxyl group, a halogen atom or an amino group which may be substituted, and salts thereof show strong antagonistic actions to angiotensin II, thus being useful as therapeutics for cardiovascular diseases.

1 Claim, No Drawings propoxy, isopropoxy, butoxy, t-butoxy, etc.), lower ($C_{1-4}$) alkoxycarbonyl (e.g. methoxycarbonyl, ethoxycarbonyl, etc.) and phenyl; the substituents of the aryl groups or the aryl groups of the aralkyloxy groups represented by $R^1$ or $R^2$ include hydroxyl, halogen (e.g. F, Cl, Br, etc.), lower($C_{1-4}$) alkyl (e.g. methyl, ethyl, propyl, etc ), lower($C_{1-4}$) alkoxy (e.g. methoxy, ethoxy, methylenedioxy, etc.), nitro, cyano, carboxyl, lower($C_{1-4}$) alkoxycarbonyl (e.g. methoxycarbon-yl, ethoxycarbonyl, etc.), amino which may be substituted (e.g. methylamino, ethylamino, etc.), and carbamoyl which may be substituted (e.g. methylaminocarbonyl, ethylaminocarbonyl, etc.). The substituents may be present at the ortho-, meta-, or para-position of the aryl group. The number of the substituents is desirably 1 or 2.

$R^1$ and $R^2$ may be bound to each other so that

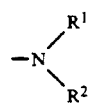

may form ah alicyclic amino group (e.g. pyrrolidino, piperidino, piperazino, morpholino, etc.), which may be substituted by lower ($C_{1-4}$) alkyl optionally substituted by one to two phenyl groups.

The compounds in which D is a hydroxyl group or a halogen atom are useful as the starting substance for the synthesis of the compounds in which D is an alkoxy group or an amino group which may be substituted.

Among the compounds represented by the formula (I), those in which the tetrazolyl (Tet) as the substituent in the biphenyl group has been replaced by cyano are useful as synthetic intermediates.

Among the compounds represented by the formula (I) described above [Compounds (I)], those represented by the formula:

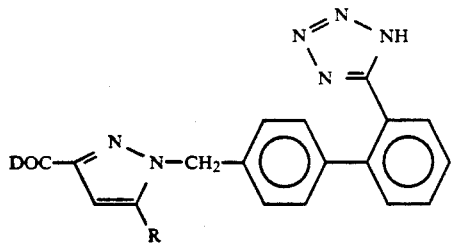

wherein R is propyl or butyl, D is a lower($C_{1-4}$) alkoxy such as methoxy, propoxy, isopropoxy, butoxy, or t-butoxy, or an amino which may be substituted with a lower($C_{1-4}$) alkyl, such as amino, methylamino, ethylamino, propylamino, isopropylamino, butylamino, t-butylamino, or dimethylamino, are desirable.

Method for Production

The compounds represented by the general formula (I) can be produced for example by the methods described below.

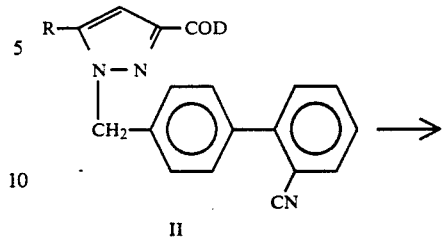

Reaction (a)

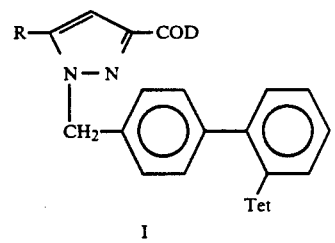

wherein R and D are the same as described above, and Tet represents tetrazolyl,

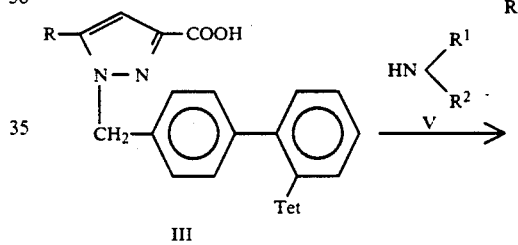

Reaction (b)

where R, $R^1$, $R^2$, and Tet are the same as described above.

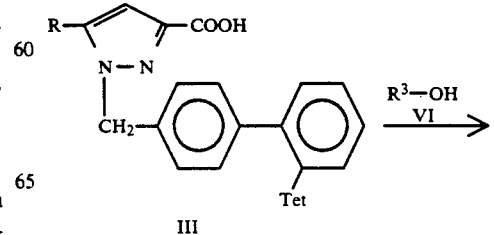

Reaction (c)

PYRAZOLE DERIVATIVE

BACKGROUND OF THE INVENTION

This invention relates to novel pyrazole derivatives and the synthetic intermediates thereof, which have excellent pharmacological actions.

In more detail, this invention relates to the compounds represented by the general formula:

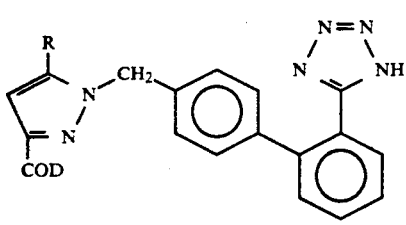

wherein R is an alkyl group and D is an alkoxy group, a hydroxyl group, a halogen atom, or an amino group which may be substituted, and the salts thereof, which have powerful antagonistic actions to angiotensin II and hypotensive actions, and thus are useful as therapeutics for diseases of the cardiovascular system, such as hypertension, heart disease, and cerebral stroke.

The renin-angiotensin system is involved in the homeostasis to control systemic blood pressure, body fluid amount, and balance among the electrolytes, together with the aldosterone system. The relation between the renin-angiotensin system and hypertension has been clarified based on the fact that an inhibitor of an angiotensin converting enzyme (ACE inhibitor) which produces angiotensin II having potent vasoconstrictive action has been developed. Because angiotensin II elevates blood pressure via the angiotensin II receptors on the cellular membrane, the antagonist of angiotensin II, like an ACE inhibitor can be used for the treatment of hypertension. Many angiotensin II-related substances, such as saralasin and [Sar$^1$, Ala$^8$] AII, have been reported to have potent angiotensin II antagonism. However, peptide antagonists have been reported to have short duration of the action after parenteral administration and to be ineffective after oral administration [M. A. Ondetti and D. W. Cushman, Annual Reports in Medicinal Chemistry, 13, 82-91 (1978)].

Non-peptide angiotensin II antagonists include imidazole derivatives having angiotensin II antagonism disclosed in Japanese Unexamined Patent Publication Nos. 71073/1981, 71074/1981, 92270/1982, 157768/1983, 23868/1988, and 117876/1989, A. T. Chiu et al., Eur. J. Pharm., 157, 13 (1988), P. C. Wong et al., J. Pharmacol. Exp. Ther., 247, 1 (1988), and P. C. Wong et al., Hypertension, 13, 489 (1989), and pyrazole derivatives having angiotensin II antagonism reported in European Unexamined Patent Publication No. 0323841.

However, the compounds represented by the formula (I) wherein R is an alkyl group and D is an alkoxy group, a hydroxyl group, a halogen atom, or an amino group which may be substituted have not been disclosed in the literature.

DETAILED DESCRIPTION

As the result of search for compounds useful as therapeutics for cardiovascular diseases such as hypertension, heart disease, and cerebral stroke, the present inventors succeeded in production of pyrazole derivatives excellent in angiotensin II antagonism, and finally have completed this invention.

That is, the present invention relates to the compounds represented by the formula:

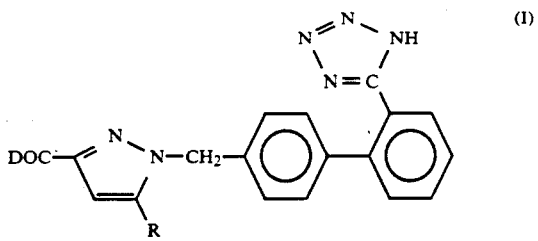

wherein R is an alkyl group and D is an alkoxy group, a hydroxyl group, a halogen atom, or an amino group which may be substituted, and the pharmaceutically acceptable salts thereof.

In the general formula (I) the alkyl group represented by R includes straight chain or branched lower alkyl groups having about 3 to about 5 carbon atoms, such as propyl, isopropyl, butyl, isobutyl, sec-butyl, t-butyl, pentyl, and isopentyl.

Alkoxy groups represented by D include lower($C_{1-4}$) alkoxy groups (e.g. methoxy, ethoxy, propoxy, isopropoxy, butoxy, t-butoxy), and the said alkoxy groups may be fluorinated with 1-3 fluorine atoms; fluorinated lower($C_{1-4}$) alkoxy groups are exemplified by trifluoroethoxy group, and the said alkoxy groups may aminated; aminated lower ($C_{1-4}$) alkoxy groups are exemplified by the formula:

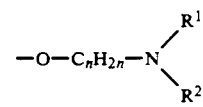

wherein n is an integer of 1 to 4 and $R^1$ and $R^2$ are as defined below.

Halogen atoms represented by D include chlorine and bromine atoms.

Amino groups represented by D which may be substituted include the group represented by the formula:

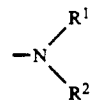

wherein $R^1$ and $R^2$ are the same or different, being selected among hydrogen atom, lower($C_{1-8}$) alkyl groups which may be substituted (e.g. methyl, ethyl, propyl, isopropyl, butyl, sec-butyl, t-butyl, hexyl, octyl, trifluoroethyl), aryl groups which may be substituted (e.g. phenyl), aralkyloxy groups which may be substituted (e.g. phenyl-lower($C_{1-4}$) alkyloxy groups such as benzyloxy group), lower($C_{3-6}$) cycloalkyl groups which may be substituted (e.g. cyclopropyl, cyclobutyl, cyclopentyl, cyclohexyl, indan-2-yl), and heterocyclic groups which may be substituted (e.g. heterocyclic groups such as furyl, thienyl, and pyridyl which may be substituted with methyl, methoxy, amino, dimethylamino, or halogen); the substituents for the lower($C_{1-8}$) alkyl groups represented by $R^1$ or $R^2$ include 1 to 3 halogen atoms (e.g. F, Cl, Br, etc.), carboxyl, lower($C_{1-\alpha}$) alkoxy groups (e.g. methoxy, ethoxy,

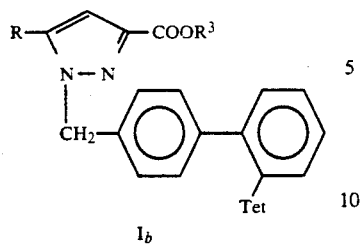

$I_b$ wherein R and Tet are the same as described above, and $R^3$ is a lower alkyl group.

The starting compounds (II) and (III) used in the reactions (a), (b), and (c) can be synthesized by the reactions described below using, as the starting substance, the compound (VI) synthesized according to the method described in the following literature or similar methods.

(1) T. L. Jacobs "Heterocyclic Compounds", Vol. 5, ed. by R. C. Elderfield, 1957, pp. 45-161, (2) D. Libermann et al., Bull. Soc. Chim. France, 1958, 687 (CA, 52, 20147d), (3) H. A. Dewald et al., J. Med. Chim., 16, 1346 (1973).

Reaction (d)

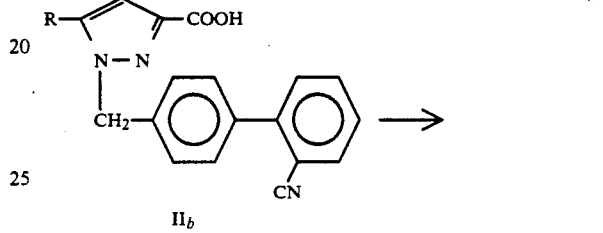

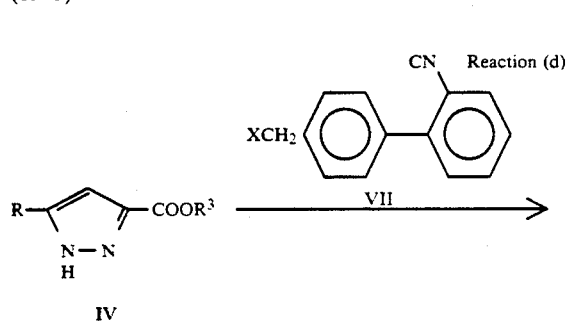

wherein R is the same as described above, $R^3$ is a lower alkyl group, and X represents a halogen atom.

Reaction (e)

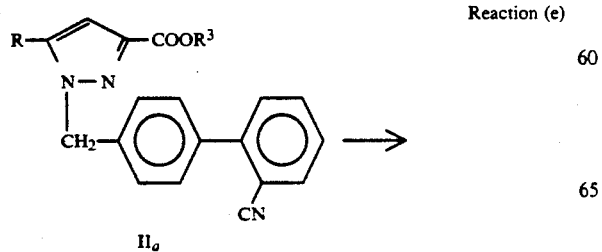

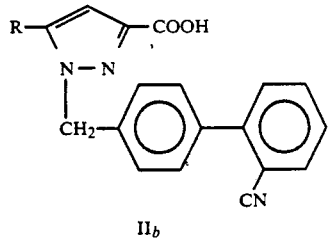

$II_b$ wherein R and $R^3$ are the same as described above.

Reaction (f)

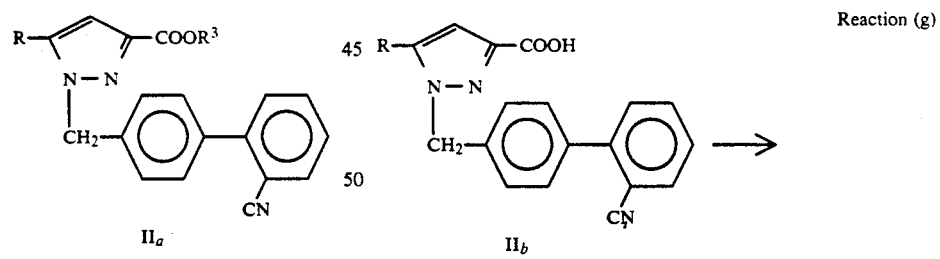

wherein R and Tet are the same as described above.

Reaction (g)

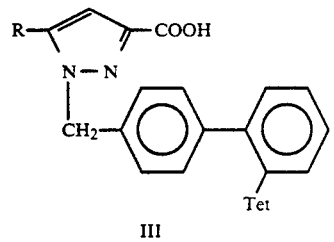

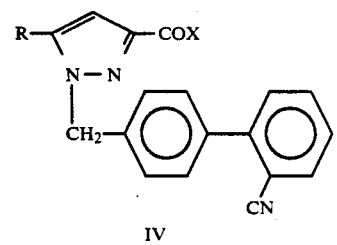

wherein R is the same as described above, and X represents a halogen atom. Reaction (h)

Reaction (h)

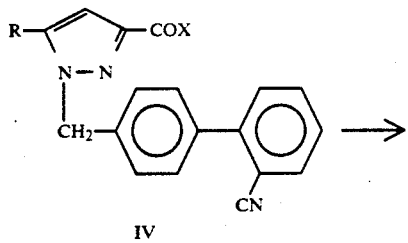
IV

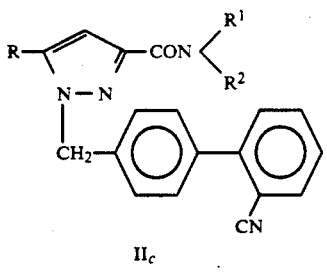
II$_c$ wherein R, R$^1$, and R$^2$ are the same as described above, and X represents a halogen atom. Reaction (i)

Reaction (i)

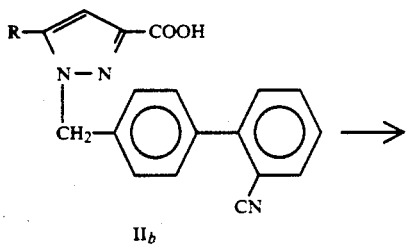
II$_b$

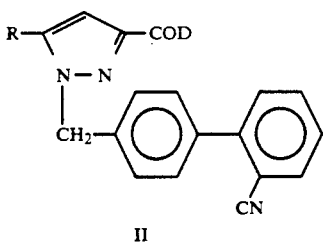
II wherein R and D are the same as described above.

The reaction (a) consists in the reaction of the cyano group, a substituent on the benzene ring, with one of various azides, to form a tetrazole derivative (I).

The reaction is conducted by using the compound (II) and an azide compound in a molar ratio of 1 mole to 1 to 3 moles usually in a solvent such as dimethylformamide, dimethylacetamide, toluene, and benzene.

The azides include trialkyltin azides, triphenyltin azides, and hydrazoic acid.

When an organic tin azide compound is to be used, the reaction is allowed to reflux in toluene or in benzene for about 10 to 30 hours. When hydrazoic acid is to be used, about 2 moles each of sodium azide and ammonium chloride are used for one mole of the compound (II) and the reaction is allowed to proceed in dimethylformamide at about 100° to 130° C. for about 1 to 3 days. It is desirable to accelerate the reaction by addition of an appropriate amount of sodium azide and ammonium chloride.

The reaction (b) described above produces an amide (Ia) from a carboxylic acid (III) and an amine (V).

The production of an amide (Ia) from a carboxylic acid (III) and an amine (V) is usually performed via activation of the carboxyl group. For example, the production is conducted by the acid chloride method, the mixed acid anhydrides method, the dicyclohexyl carbodiimide (DDC) method, the carbodiimidazole (CDI) method, the active ester method, and the method using a phosphorus compound. Among these methods, condensation by phosphorus compounds such as diphenyl phosphorylazide (DPPA) and diethyl phosphorocyanidate (DEPC) or by oxidation-reduction system using triphenylphosphine are convenient.

For one mole of the compound (III), are used 1 to 5 moles of triphenylphosphine, 1 to 3 moles of an amine (V), 1 to 5 moles of an oxidizing agent (e.g. N-chlorosuccinimide, N-bromosuccinimide), and 2 to 10 moles of a tertiary amine (e.g. triethylamine, tributylamine) for neutralization of the acid formed during the reaction.

The reaction is usually allowed to proceed by addition of an oxidizing agent such as N-chlorosuccinimide to a solution of the carboxylic acid (III), triphenylphosphine, the amine (V), and the tertiary amine in a solvent of a halogenated hydrocarbon (e.g. chloroform, dichloroethane).

The amine (V) is selected from the amines which may be substituted, being exemplified by alkyl amines (methylamine, ethylamine, propylamine, isopropylamine, butylamine, dimethylamine, diethylamine, 2-methoxyethylamine, etc.), aralkyl amines (benzylamine, phenethylamine, etc.), aryl amines (aniline, N-methylaniline, etc.), and alicyclic amines (pyrrolidine, piperidine, morpholine, etc.).

The reaction is desirably conducted at the temperature of ice-cooling to room temperature for about 30 minutes to 2 hours.

The reaction (c) produces an ester (Ib) by esterification of the carboxylic acid (III).

The most common procedure for the reaction consists in a dehydration reaction between a carboxylic acid (III) and an alcohol (VI). This reaction, being an equilibrium reaction, is conducted by using a large excess of alcohol in the presence of a catalyst selected among mineral acids such as sulfuric acid and hydrochloric acid, organic acids such as aromatic sulfonic acids (e.g. p-toluenesulfonic acid), Lewis acids such as boron trifluoride etherate, and acidic ion exchange resins.

For one mole of the carboxylic acid (III), are used 5 to 10 moles or a large excess of alcohol. The solvent used is an aromatic hydrocarbon such as benzene or toluene, and it is desirable that the water formed is separated by azeotropic distillation in the Dean-Stark water separator. Use of a large excess of the alcohol as the solvent is also convenient. In any case, it is desirable to use one of the acid catalysts described above.

The reaction is desirably conducted at about the boiling point of the solvent for about 2 to 10 hours.

The reaction (d) described above consists in alkylation with an alkylating agent in the presence of a base.

For one mole of the compound (IV), are used 1 to 3 moles of a base and about 1 to 3 moles of an alkylating agent. The reaction is usually conducted in a solvent such as dimethylformamide, dimethylacetamide, dimethyl sulfoxide, acetonitrile, acetone, ethyl methyl ketone, dioxane, or tetrahydrofuran.

The bases used in the reaction include sodium hydroxide, potassium t-butoxide, potassium carbonate, and sodium carbonate.

The alkylating agents used in the reaction include substituted halides (e.g. chlorides, bromides, iodides), and substituted sulfonic esters (e.g. methyl p-toluenesulfonate).

The reaction conditions may be varied according to the combination of the base and the alkylating agent; the reaction is usually desirably conducted at the temperature of ice-cooling to room temperature for about 1 to 10 hours.

The alkylation produces generally a mixture of two isomers, 1-alkyl product (I) and 2-alkyl product which are different in the position of the N atom to be alkylated. However use of an ether such as dioxane or tetrahydrofuran produces selectively the desired 1-alkyl product alone, which is easily obtained in a good yield by usual methods for separation and purification.

The reaction (e) described above produces a carboxylic acid (IIb) by hydrolysis of an ester (IIa) in the presence of an alkali.

For one mole of the compound (IIa), are used about 1 to 3 moles of the alkali, and the reaction is conducted in an aqueous alcohol (methanol, ethanol, methyl cellosolve, etc.) as the solvent.

The alkalis used in the reaction include sodium hydroxide and potassium hydroxide.

The reaction is desirably conducted at room temperature to about 100° C. for about 1 to 10 hours.

The reaction (f) described above is desirably performed under conditions similar to those for the Reaction (a).

The reaction (g) produces an acid halide (IV) by treatment of a carboxylic acid (IIb) with a halogenating agent.

For one mole of the compound (IIb), are used about 1 to 5 moles of the halogenating agent, and the reaction is usually conducted in a solvent such as halogenated hydrocarbons ($CHCl_3$, $CH_2Cl_2$, $ClCH_2CH_2Cl$, etc.), ethers (tetrahydrofuran, dioxane, etc.), and aromatic compounds (benzene, toluene, etc.).

The halogenating agents used in the reaction include thionyl chloride, phosphorus oxychloride, phosphorus trichloride, and phosphorus pentachloride.

The reaction is desirably conducted at room temperature to about 100° C. for about 1 to 10 hours.

The reaction (h) produces an amide (IIc) by the treatment of an acid halide (IV) with an amine.

For one mole of the compound (IV), are used about 2 to 5 moles of the amine, and the reaction is usually conducted in a solvent such as alcohols (methanol, ethanol, etc.), and ethers (ethyl ether, tetrahydrofuran, dioxane, etc.).

The amines used in the reaction include ammonia, alkyl amines (methylamine, ethylamine, propylamine, dimethylamine, diethylamine, butylamine, etc.), aralkyl amines (benzylamine, phenethylamine, etc.), aryl amines (aniline, N-methylaniline, etc.), and alicyclic amines (morpholine, piperidine, piperazine, N-phenylpiperazine, etc.).

The acid halides used in the reaction include acid chlorides and acid bromides.

The reaction is usually conducted at the temperature of ice-cooling to room temperature for about 1 to 5 hours.

The reaction (i) is desirably conducted under conditions similar to those described for the reactions (b) and (c).

The compound (VII) among the starting compounds can be obtained by halogenomethylation of the compound (VI), which is commercially available or synthesized by the method known in the literature, by the reaction (j) according to the method described, for example, in A. A. Vansheidt et al., Khim. Nauka i Prom., 2, 799 (1957). The reaction (j) is desirably conducted by using $TiCl_4$ in more excess than usually used, for example about 3 to 6 moles, for one mole of chloromethyl methyl ether. Reaction (j)

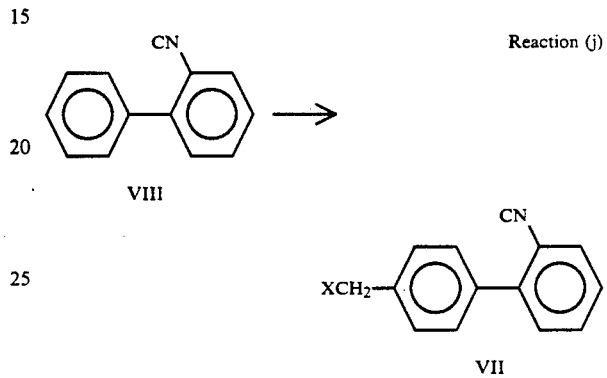

wherein X represents a halogen atom.

The compounds (I) described above can be converted into the salts thereof with physiologically acceptable acids or bases by conventional methods. Such salts include salts with inorganic acids such as hydrochlorides, sulfates, and nitrates, salts with organic acids such as acetates, oxalates, succinates, and maleates, salts with alkaline metals such as sodium salts, and potassium salts, and salts with alkaline earth metals such as calcium salts.

The compounds (I) and the salts thereof thus produced are of less toxicity, inhibit the vasoconstrictive and hypertensive effects of angiotensin II, exert a hypotensive effect in animals, in particular mammals (e.g. human, dog, rabbit, rat, etc.), and therefore they are useful as therapeutics for the cardiovascular diseases such as heart disease and cerebral stroke. The compounds (I) and the salts thereof, when used as such therapeutics, can be orally or parenterally administered as they are or in the form of powders, granules, tablets, capsules, injections, etc. prepared by mixing with appropriate pharmaceutically acceptable carriers, excipients, or diluents.

The dose varies according to the disease to be treated, symptoms, subjects, and dosing regimens, and it is desirable that a daily dose of 10 to 100 mg for oral administration or 5 to 50 mg for intravenous injection is divided into 2 to 3 when the compounds (I) and the salts thereof are to be used as the therapeutics for essential hypertension in adults.

EXAMPLES

The following Working Examples, Experimental Examples and Reference Examples explain the present invention more concretely, but it is a matter of course that the Examples should not limit the present invention.

Reference Example 1

Ethyl 2,4-dioxooctanate

To a solution of sodium (9.3 g) in ethanol (200 ml) was added dropwise a mixture of diethyl oxalate (60 g) and 2-hexanone (40.9 g) with stirring. The reaction mixture was allowed to stand at room temperature for 45 hours. To a mixture of 1N-hydrochloric acid (500 ml) and hexane (500 ml) was added dropwise the reaction mixture with stirring vigorously. After the addition, water (500 ml) was added. The organic layer was washed with water (100 ml ×3), dried, and the solvent was removed by evaporation in vacuo. The residue was distilled under reduced pressure and the distillate at the boiling point of 110° to 111° C. (6 mmHg) was collected to give the desired product (57 g, 70%).

NMR (90 MHz, CDCl$_3$)δ: 0.90 (3H, t), 1.17–1.80 (7H, m), 2.47 (2H, t), 4.33 (2H, q), 6.37 (1H, s), 13.70–15.13 (1H, brs)

IR (Neat)cm$^{-1}$: 2970, 2940, 2875, 1750, 1735, 1640, 1590, 1270, 1120, 1110, 1020, 1015.

In the same way as in the Reference Example 1, the following compounds were produced.

REFERENCE EXAMPLE 2

Ethyl 2,4-dioxoheptanate was obtained as a syrup in a 76% yield.

$^1$H-NMR (CDCl$_3$)δ: 0.97 (3H, t), 1.38 (3H, t), 1.70 (2H, m), 2.48 (2H, t), 4.36 (2H, q), 6.37 (1H, s)

REFERENCE EXAMPLE 3

Ethyl 2,4-dioxononanate was obtained as a syrup in a 94% yield.

$^1$H-NMR (CDCl$_3$)δ: 0.90 (3H, t), 1.28–1.42 (7H, m), 1.60–1.75 (2H, m), 2.49 (2H, t), 4.35 (2H, q), 6.34 (1H, s)

REFERENCE EXAMPLE 4

Ethyl 5-butylpyrazole-3-carboxylate

To a solution of ethyl 2,4-dioxooctanate (3.4 g) in alcohol (15 ml) was added hydrated hydrazine (860 mg) in small portions with stirring and the mixture was stirred at ambient temperature for 30 minutes. The reaction mixture wa concentrated under reduced pressure. To the residue were added dilute hydrochloric acid (20 ml) and hexane (50 ml), and the mixture was partitioned. The organic layer was concentrated under reduced pressure to give the desired product as an oil (3.17 g, 94%).

NMR (90 NHz, CDCl$_3$)δ: 0.90 (3H, t), 1.13–1.80 (6H, m), 2.70 (2H, t), 4.37 (2H, q), 6.60 (1H, s), 10.57 1 (1N, brs)

IR (Neat)cm$^{-1}$: 3190, 3140, 3090, 2930, 2865, 1725, 1460, 1235, 1155, 1020.

According to the Reference Example 4, the following compounds were synthesized.

REFERENCE EXAMPLE 5

Ethyl 5-propylpyrazole-3-carboxylate m.p. : syrup
yield: 95%

$^1$H-NMR (CDCl$_3$)δ: 0.93 (3H, t), 1.34 (3H, t), 1.67 (2H, m), 2.66 (2H, t), 4.34 (2H, q), 6.58 (1H, s)

REFERENCE EXAMPLE 6

Ethyl 5-pentylpyrazole-3-carboxylate m.p. : syrup
yield: 95%

$^1$H-NMR (CDCl$_3$)δ: 0.86 (3H, t), 1.1–1.8 (12H, m), 2.67 (2H, t), 4.34 (2H, q), 6.59 (1H, s)

REFERENCE EXAMPLE 7

Ethyl 5-butyl-1-[(2,-cyanobiphenyl-4-yl)methyl]pyrazole-3-carboxylate

Sodium hydride (60% in oil, 88 mg) was washed with hexane, to which tetrahydrofuran (THF) (8 ml) was added. To the mixture were added ethyl 5-butyl-pyrazole-3-carboxylate (431 mg) and 4-(2'-cyanophenyl)benzyl bromide (599 mg) with stirring, and the mixture was allowed to stir at room temperature for 13 hours. The reaction mixture was concentrated under reduced pressure, and the residue was partitioned with water (20 ml) and ethyl acetate (50 ml). The organic layer was washed with water, dried, and concentrated to dryness. The resultant residue was purified by column chromatography on silica gel to give the desired product as a light yellow syrup (730 mg, 86%).

NMR (90 MHz, CDCl$_3$)δ: 0.87 (3H, t), 1.07–1.73 (7H, m), 2.53 (2H, t), 4.40 (2H, q), 5.47 (2H, s), 6.67 (1H, s), 7.13–7.83 (8H, m)

IR (Neat)cm$^{-1}$: 2970, 2940, 2875, 2220, 1730, 1480, 1445, 1220, 765

In the same way as in the Reference Example 7, the following compounds were synthesized.

REFERENCE EXAMPLE 8

Ethyl 5-pentyl-1-[(2,-cyanobiphenyl-4-yl)methyl]pyrazole-3-carboxylate m.p. : syrup
yield: 48%

$^1$-NMR (CDCl$_3$)δ: 0.86 (3H, t), 1.25–1.33 (4H, m), 1.41 (3H, t), 1.55–1.62 (2H, m), 2.53 (2H, t), 4.43 (2H, q), 5.46 (2H, s), 6.68 (1H, s), 7.21 (2H, d), 7.41–7.54 (4H, m), 7.66 (1H, m), 7.76 (1H, m)

REFERENCE EXAMPLE 9

Ethyl 5-propyl-1-[(2'-cyanobiphenyl-4-yl)methyl]pyrazole-3-carboxylate m.p. : syrup
yield: 77%

$^1$H-NMR (CDCl$_3$)δ: 0.95 (3H, t), 1.41 (3H, t), 1.54–1.72 (2H, m), 2.51 (2H, t), 4.43 (2H, q), 5.46 (2H, s), 6.68 (1H, s), 7.21 (2H, d), 7.41–7.54 (4H, m), 7.65 (1H, m), 7.76 (1H, d)

REFERENCE EXAMPLE 10

5-Butyl-1-[(2'-cyanobiphenyl-4-yl)methyl]pyrazole-3-carboxylic acid

To a solution of ethyl 5-butyl-1-[(2'-cyanobiphenyl-4-yl)methyl]pyrazole-3-carboxylate (5.75 g) in methanol (100 ml) was added 2N-NaOH (15 ml) and the mixture was allowed to stand at room temperature for 2 hours. Water (10 ml) was added and methanol was evaporated under reduced pressure. The mixture was made acidic by addition of 2N-HCl, followed by extraction with The symbols used in this specification mean: s: singlet, d: doublet, t: triplet, q: quartet, brs: broad singlet, Tet: tetrazolyl ether. The organic layer was washed with water (20 ml×2), dried, and concentrated under reduced pressure, to give a colorless syrup. The syrup was recrystallized from chloroform to give colorless crystals (4.3 g, 81%).

m.p. 192°–194° C.
$^1$H-NMR (90 MHz, CDCl$_3$)δ: 0.90 (3H, t), 1.13–1.97 (4H, m), 2.57 (2H, t), 5.50 (2H, s), 6.79 (1H, s), 7.20–7.80 (8H, m)
IR (Neat)cm$^{-1}$: 2965, 2925, 2865, 2220, 1720, 1480, 1460, 1450, 1385, 1225, 765

REFERENCE EXAMPLE 11

5-Butyl-1-[(2'-cyanobiphenyl-4-yl)methyl]-pyrazole-3-carbonyl chloride

To a solution of ethyl 5-butyl-1-[(2'-cyanobiphenyl-4-yl)methyl]pyrazole-3-carboxylate (1.2 g) in methanol (5 ml) was added 2N-NaOH (3 ml) and the mixture was allowed to stand at room temperature for 14 hours. Water (10 ml) was added and methanol was removed by evaporation in vacuo. The resultant aqueous solution was washed with ether (30 ml×2). The aqueous solution was made acidic by addition of 2N-hydrochloric acid, followed by extraction with methylene chloride. The oily product obtained by evaporation of the solvent was dissolved in benzene (15 ml), to which was added thionyl chloride (1.5 ml), and the mixture was refluxed for 2 hours. The reaction mixture was concentrated under reduced pressure to give the 3-carbonyl chloride as a yellow syrup (0.98 g, 90%).

IR (Neat)cm$^{-1}$: 2965, 2940, 2870, 2220, 1765, 1480, 1415, 1145, 1030

REFERENCE EXAMPLE 12

5-Butyl-1-[(2'-cyanobiphenyl-4-yl)methyl-]-N-isopropylpyrazole-3-carboxamide

To a solution of 5-butyl-1-[(2'-cyanobiphenyl-4-yl)methyl]pyrazole-3-carbonyl chloride (550 mg) in dichloromethane (5 ml) were added isopropylamine (0.2 ml) and pyridine (0.2 ml), and the mixture was stirred at room temperature for 0.5 hours. The mixture was then evaporated to dryness under reduced pressure, and the residue was shaken with a mixture of 0.1 N hydrochloric acid (50 ml), dichloromethane (15 ml), and ether (60 ml). The mixture was allowed to separate into layers. The organic layer was washed with an aqueous solution of sodium bicarbonate and dried over anhydrous magnesium sulfate, followed by evaporation of the solvent to give a light yellow syrup (550 mg, 98%).

$^1$H-NMR (CDCl$_3$)δ: 0.83 (3H, t), 1.03–1.73 (10H, m), 2.53 (2H, t), 4.30 (1H, m), 5.37 (2H, s), 6.63 (1H, s), 6.73 (1H, brs), 7.10–7.83 (8H, m)
IR (Neat)cm$^{-1}$: 3425, 3325, 2975, 2950, 2875, 2220, 1660, 1525, 1480, 1450, 1385, 1225, 820, 765

In the same way as in the Reference Example 12, the following compounds were synthesized.

REFERENCE EXAMPLE 13

5-Butyl-1-[(2'-cyanobiphenyl-4-yl)methyl]-N-methylpyrazole-3-carboxamide m.p. : syrup
yield: 88%
$^1$H-NMR (CDCl$_3$)δ: 0.87 (3H, t), 1.13–1.77 (4H, m), 2.53 (2H, t), 5.33 (2H, s), 5.43 (1H, brs), 6.63 (1H, s), 6.73 (1H, brs), 7.10–7.83 (8H, m)

REFERENCE EXAMPLE 14

5-Butyl-1-[(2'-cyanobiphenyl-4-yl)methyl]-N-ethylpyrazole-3-carboxamide m.p : syrup
yield: 65%
$^1$H-NMR (CDCl$_3$)δ: 0.88 (3H, t), 1.21–1.44 (5H, m), 1.52–1.67 (2H, m), 2.55 (2H, t), 3.40–3.54 (2H, m), 5.36 (2H, s), 6.67 (1H, s), 6.87 (1H, t), 7.16 (2H, d), 7.41–7.55 (4H, m), 7.61–7.69 (1H, m), 7.77 (1H, d)

REFERENCE EXAMPLE 15

5-Butyl-1-[(2'-cyanobiphenyl-4-yl)methyl]-N-propylpyrazole-3-carboxamide m.p. : syrup
yield: quantitative
$^1$H-NMR (CDCl$_3$)δ: 0.88 (3H, t), 0.98 (3H, t), 1.35 (2H, m), 1.52–1.69 (4H, m), 2.55 (2H, t), 3.41 (2H, q), 5.36 (2H, s), 6.67 (1H, s), 6.91 (1H, t), 7.16 (2H, d), 7.42–7.55 (4H, m), 7.61–7.70 (1H, m), 7.77 (1H, d)

REFERENCE EXAMPLE 16

5,N-Dibutyl-1-[(2'-cyanobiphenyl-4-yl)methyl]-pyrazole-3-carboxamide m.p. : syrup
yield: quantitative
$^1$H-NMR (CDCl$_3$)δ: 0.88 (3H, t), 0.95 (3H, t), 1.26–1.46 (4H, m), 1.50–1.67 (4H, m), 2.54 (2H, t), 3.43 (2H, q), 5.36 (2H, s), 6.67 (1H, s), 6.88 (1H, t), 7.16 (2H, d), 7.41–7.55 (4H, m), 7.61–7.69 (1H, m), 7.77 (1H, d)

REFERENCE EXAMPLE 17

5-Butyl-N-t-butyl-1-[(2'-cyanobiphenyl-4-yl)methyl]-pyrazole-3-carboxamide m.p. : syrup
yield: quantitative
$^1$H-NMR (CDCl$_3$)δ: 0.87 (3H, t), 1.34 (2H, m], 1.47 (9H, s), 1.50–1.65 (2H, m), 2.52 (2H, t), 5.35 (2H, s), 6.63 (1H, s), 6.77 (1H, s), 7.15 (2H, d), 7.41- 7.55 (4H, m), 7.61–7.69 (1H, m), 7.75–7.78 (1H, m)

REFERENCE EXAMPLE 18

5-Butyl-1-[(2'-cyanobiphenyl-4-yl)methyl]-N-octyl-pyrazole-3-carboxamide m.p. : syrup
yield: quantitative
$^1$H-NMR CDCl$_3$)δ: 0.85–0.92 (6H, m), 1.20–1.44 (2H, 1.52–1.68 (4H, m), 2.54 (2H, t), 3.41 (2H, q), 5.36 (2H, s), 6.67 (1H, s), 6.88 (1H, t), 7.16 (2H, d), 7.41–7.55 (4H, m), 7.61–7.70 (1H, m), 7.77 (1H, d)

REFERENCE EXAMPLE 19

5-Butyl-1-[(2'-cyanobiphenyl-4-yl)methyl]-N-cyclohexylpyrazole-3-carboxamide m.p. : syrup
yield: quantitative
$^1$H-NMR (CDCl$_3$)δ: 0.88 (3H, t), 1.14–1.80 (12H, m), 1.99–2.05 (2H, m), 2.53 (2H, t), 3.94 (1H, m), 5.36 (2H, s), 6.67 (1H, s), 6.77 (1H, d), 7.16 (2H, d), 7.41–7.55 (4H, m), 7.61–7.70 (1H, m), 7.77 (1H, d)

REFERENCE EXAMPLE 20

N-Benzyl-5-butyl-1-[(2'-cyanobiphenyl-4-methyl]-pyrazole-3-carboxamide m.p. : syrup yield: quantitative ¹H-NMR (CDCl₃)δ: 0.89 (3H, t), 1.35 (2H, m), 1.52–1.67 (2H, m), 2.55 (2H, t), 4.63 (2H, d), 5.34 (2H, s), 6.71 (1H, s), 7.13–7.60 (12H, m), 7.61–7.69 (1H, m), 7.76 (1H, d)

REFERENCE EXAMPLE 21

5-Butyl-1-[(2'-cyanobiphenyl-4-yl)methyl]-N-phenylpyrazole-3-carboxamide m.p. : syrup yield: quantitative ¹H-NMR (CDCl₃)δ: 0.90 (3H, t), 1.37 (2H, m), 1.54–1.69 (2H, m), 2.58 (2H, t), 5.41 (2H, s), 6.76 (1H, s), 7.07–7.78 (13H, m), 8.73 (1H, s)

REFERENCE EXAMPLE 22

5-Butyl-1-[(2'-cyanobiphenyl-4-yl)methyl]-N-indan-2-yl)pyrazole-3-carboxamide m.p. : syrup yield: quantitative ¹H-NMR (CDCl₃)δ: 0.88 (3H, t), 1.34 (2H, m), 1.51–1.66 (2H, m), 2.53 (2H, t), 2.95 (2H, q), 3.41 (2H, q), 4.85–5.02 (1H, m), 5.33 (2H, s), 6.68 (1H, s), 7.05–7.25 (7H, m), 7.40–7.53 (4H, m), 7.60–7.68 (1H, m), 7.76 (1H, d)

REFERENCE EXAMPLE 23

=-Butyl-1-[(2'-cyanobiphenyl-4-yl)methyl]-N-(2-methoxyethyl)pyrazole-3-carboxamide m.p. : syrup yield: 82%

¹H-NMR CDCl₃)δ: 0.87 (3H, t), 1.10–1.77 (4H, m), 2.53 (2H, t), 3.37 (3H, s), 3.43–3.73 (4H, m), 5.33 (2H, s), 6.63 (1H, s), 7.10–7.80 (8H, m)

REFERENCE EXAMPLE 24

Isopropyl 5-butyl-1-[(2'-cyanobiphenyl-4-yl)methyl]pyrazole-3-carboxylate m.p. syrup yield: 92%

¹H-NMR (CDCl₃)δ: 0.87 (3H, t), 1.13–1.83 (10H, m), 2.50 (2H, t), 5.30 (1H, m), 5.47 (2H, s), 6.63 (1H, s), 7.13–7.80 (8H, m)

REFERENCE EXAMPLE 25 t-Butyl 5-butyl-1-[(2'-cyanobiphenyl-4-yl)methyl]-pyrazole-3-carboxylate m.p. : syrup yield: 75%

¹H-NMR (CDCl₃)δ: 0.87 (3H, t), 1.13–1.73 (13H, m), 2.50 (2H, t), 5.43 (2H, t), 5.43 (2H, s), 6.53 (1H, s), 7.13–7.80 (8H, m)

REFERENCE EXAMPLE 26

5-Butyl-1-[(2'-cyanobiphenyl-4-yl)methyl]-N-(3-ethoxycarbonylbenzyl)pyrazole-3-carboxamide m.p. : syrup yield: 98%

¹H-NMR (90MHz, CDCl₃)δ: 0.87 (3H, t), 1.07–1.80 (7H,m), 2.53 (2H, t), 4.03–4.40 (2H, m), 5.37 (2H, s), 5.43 (1H, d), 5.77 (1H, d), 6.63 (1H, s), 7.13–7.87 (13H, m)

IR(CHCl₃)cm⁻¹: 3420, 3000, 2965, 2940, 2870, 2220, 1740, 1665, 1525, 1450, 1310, 1175

REFERENCE EXAMPLE 27

5-Butyl-1-[(2'-cyanobiphenyl-4-yl)methyl]-N-(3-ethoxycarbonylphenyl)pyrazole-3-carboxamide m.p. : syrup yield: 95%

¹H-NMR (90MHz, CDCl₃)δ: 0.90 (3H, t), 1.10–1.80 (7H,m), 2.60 (3H, t), 4.40 (2H, q), 5.40 (2H, s), 6.77 (1H, s), 7.17–7.87 (9H, m), 8.07–8.20 (3H, m), 8.87 (1H, brs)

IR(Neat)cm⁻¹: 3380, 3325, 2960, 2930, 2870, 2220, 1720, 1680, 1590, 1550, 1530, 1440, 1300, 1285, 1190

WORKING EXAMPLE 1

Ethyl 5-butyl-1-[[2'-(1H-tetrazol-5-yl)biphenyl-4-yl]methyl]-pyrazole-3-carboxylate To a solution of ethyl 5-butyl-1-[(2'-cyanobiphenyl-4-yl)methyl]pyrazole-3-carboxylate (730 mg) in dimethylformamide (10 ml) were added sodium azide (1.3 g) and ammonium chloride (1.07 g) and the mixture was stirred at 110°–115° C. for 72 hours. Insoluble materials were filtered off, and the filtrate was concentrated to dryness. To the residue were added 0.5 N-hydrochloric acid (40 ml) and ether (100 ml) for partitioning, and the organic layer was washed with water, dried, and concentrated to dryness. The residue was purified by column chromatography on silica gel to give the desired product as a colorless powder (470 mg, 58%).

Elemental analysis for $C_{28}H_{34}N_6O_2$

| Elemental analysis for $C_{28}H_{34}N_6O_2$ | | |
|---|---|---|
| C (%) | H (%) | N (%) |
| Calc.: 66.96; | 6.09; | 19.52 |
| Found: 66.67; | 6.09; | 19.38 |

NMR (90 MHz, CDCl₃-CD₃OD)δ: 0.90 (3H, t), 1.17–1.77 (7H, m), 2.57 (2H, t), 4.37 (2H, q), 5.33 (2H, s), 6.67 (1H, s), 6.97–7.20 (4H, m), 7.37–7.70 (3H, m), 7.80–7.97 (1H, m)

IR (Nujol)cm⁻¹: 1715, 1215, 1020, 770, 755

In the same way as in the Working Example 1, the following compounds were obtained.

WORKING EXAMPLE 2

5,N-Dibutyl-1-[[2'-(1H-tetrazol-5-yl)biphenyl-4-yl]methyl]pyrazole-3-carboxamide m.p. : 116°–117° C.

yield: 40%

Elemental analysis for $C_{26}H_{31}N_7O$

|  | C (%) | H (%) | N (%) |
|---|---|---|---|
| Calc.: | 68.25; | 6.83; | 21.43 |
| Found: | 68.06; | 6.74; | 21.60 |

¹H-NMR (CDCl₃)δ: 0.86 (3H, t), 0.90 (3H, t), 1.24–1.56 (8H, m), 2.44 (2H, t), 3.28 (2H, q), 5.20 (2H, s), 6.46 (1H, s), 6.88 (2H, d), 7.01–7.07 (3H, m), 7.39 (1H, q), 7.46 (1H, m), 7.56 (1H, m), 7.80 (1H, q)

WORKING EXAMPLE 3

5-Butyl-N-t-butyl-1-[[2'-(1H-tetrazol-5-yl)biphenyl-4-yl]methyl]pyrazole-3-carboxamide m.p. : 105°–108° C.
yield: 68%
Elemental analysis for $C_{26}H_{31}N_7O.3/1H_2O$

|  | C (%) | H (%) | N (%) |
|---|---|---|---|
| Calc.: | 67.45; | 6.88; | 21.18 |
| Found: | 67.60; | 6.75; | 21.20 |

$^1$H-NMR (CDCl$_3$)δ: 0.85 (3H, t), 1.21–1.57 (4H, m), 1.42 (9H, s), 2.44 (2H, t), 5.23 (2H, s), 6.43 (1H, s), 6.80 (1H, s), 6.91 (2H, d), 7.06 (2H, d), 7.38 (1H, q), 7.44–7.61 (2H, m), 7.87 (1H, q)

WORKING EXAMPLE 4

5-Butyl-N-n-octyl-1-[[2'-(1H-tetrazol-5-yl)biphenyl-4-yl]methyl]pyrazole-3-carboxamide m.p. : 45°–50° C.
yield: 46%
Elemental analysis for $C_{30}N_{39}N_7O.0.3H_2O$

|  | C (%) | H (%) | N (%) |
|---|---|---|---|
| Calc.: | 69.42; | 7.69; | 18.89 |
| Found: | 69.51; | 7.75; | 18.69 |

$^1$H-NMR (CDCl$_3$)δ: 0.86 (3H, t), 1.2–1.6 (16H, m), 2.44 (2H, t), 3.27 (2H, q), 5.21 (2H, s), 6.46 (1H, s), 6.89 (2H, d), 6.98–7.05 (3H, m), 7.37–7.60 (3H, m), 7.83 (1H, d)

WORKING EXAMPLE 5

5-Butyl-N-cyclohexyl-1-[[2'-(1H-tetrazol-5-yl)biphenyl-4-yl]methyl]pyrazole-3-carboxamide m.p. : 139°–140° C.
yield: 46%
Elemental analysis for $C_{28}H_{33}N_7O.0.9H_2O$

|  | C (%) | H (%) | N (%) |
|---|---|---|---|
| Calc.: | 67.28; | 7.02; | 19.62 |
| Found: | 67.47; | 6.73; | 19.58 |

$^1$H-NMR (CDCl$_3$)δ: 0.87 (3H, t), 1.12–1.78 (12H, m), 1.86–1.92 (2H, m), 2.44 (2H, t), 3.74–3.89 (1H, m), 5.25 (2H, s], 6.56 (1H, s), 6.81 (1H, d), 6.93 (2H, d), 7.08 (2H, d), 7.40 (1H, q), 7.47–7.62 (2H, m), 7.92 (1H, q)

WORKING EXAMPLE 6

N-Benzyl-5-butyl-1-[[2'-(1H-tetrazol-5-yl)biphenyl-4-yl]methyl]pyrazole-3-carboxamide m.p. : 188°–189° C. (decompose)
yield: 82%
Elemental analysis for $C_{29}H_{29}N_7O.\frac{1}{2}H_2O$

|  | C (%) | H (%) | N (%) |
|---|---|---|---|
| Calc.: | 69.58; | 6.04; | 19.59 |
| Found: | 69.55; | 5.85; | 19.48 |

$^1$H-NMR (CDCl$_3$)δ: 0.88 (3H, t), 1.23–1.42 (2H, m), 1.46–1.61 (2H, m), 2.48 (2H, t), 4.89 (2H, d), 5.21 (2H, s), 6.54 (1H, s), 6.94 (2H, d), 7.08 (2H, d), 7.19–7.30 (6H, m), 7.39 (1H, q), 7.46–7.62 (2H, m), 7.94 (1H, q)

WORKING EXAMPLE 7

5-Butyl-N-phenyl-1-[[2'-(1H-tetrazol-5-yl)biphenyl-4-yl]methyl]pyrazole-3-carboxamide m.p. : 103°–105° C.
yield: 66%
Elemental analysis for $C_{28}H_{27}N_7O.0.4H_2O$

|  | C (%) | H (%) | N (%) |
|---|---|---|---|
| Calc.: | 69.37; | 5.78; | 20.23 |
| Found: | 69.60; | 5.72; | 19.95 |

$^1$H-NMR CDCl$_3$δ: 0.86 (3H, t), 1.22–1.40 (2H, m), 1.44–1.59 (2H, m), 2.46 (2H, t), 5.19 (2H, s), 6.60 (1H, s), 6.89 (2H, d), 6.99–7.13 (3H, m), 7.25–7.54 (5H, m), 7.60 (2H, d), 7.84 (1H, q)

WORKING EXAMPLE 8

5-Butyl-N-(indan-2-yl)-1-[[2'-(1H-tetrazol-5-biphenyl-4-yl]methyl]pyrazole-3-carboxamide m.p. : 194°–195° C.
yield: 25%
Elemental analysis for $C_{31}H_{31}N_7O.\frac{1}{2}H_2O$

|  | C (%) | H (%) | N (%) |
|---|---|---|---|
| Calc.: | 70.90; | 6.12; | 18.62 |
| Found: | 70.62; | 5.95; | 18.48 |

$^1$H-NMR (CDCl$_3$)δ: 0.88 (3H, t), 1.23–1.40 (2H, m), 1.45–1.60 (2H, m), 2.46 (2H, t), 2.87 (2H, q), 3.32 (2H, q), 4.72–4.83 (1H, m), 5.23 (2H, s), 6 52 (1H, s), 6.95 (2H, d), 7.06–7.25 (7H, m), 7.39 (1H, q), 7.48–7.64 (2H, m), 7.99 (1H, q)

WORKING EXAMPLE 9

O-Benzyl-5-butyl-1-[[2'-(1H-tetrazol-5-yl)biphenyl-4-yl]methyl]pyrazole-3-carbohyiroxamicacid m.p. : 191°–193° C.
yield: 25%
Elemental analysis for $C_{29}H_{29}N_2O_2.0.3H_2O$

|  | C (%) | H (%) | N (%) |
|---|---|---|---|
| Calc.: | 67.90; | 5.82; | 19.11 |
| Found: | 67.95; | 5.81; | 18.91 |

$^1$H-NMR (CDCl$_3$)δ: 0.88 (3H, t), 1.17–1.43 (2H, m), 1.48–1.63 (2H, m), 2.51 (2H, t), 4.91 (2H, s), 5.22 (2H, s), 6.57 (1H, s), 6.89 (2H, d), 7.07 (2H, d), 7.30–7.42 (6H, m), 7.48–7.62 (2H, m), 7.98 (1H, q), 9.55 (1H, brs)

WORKING EXAMPLE 10

5-Butyl-N,N-dimethyl-1-[[2'-(1H-tetrazol-5-yl)biphenyl-4-yl]methyl]pyrazole-3-carboxamide m.p. : syrup
yield: 51%
Elemental analysis for $C_{24}H_{27}N_7O.\frac{1}{2}H_2O$

|  | C (%) | H (%) | N (%) |
|---|---|---|---|
| Calc.: | 65.73; | 6.44; | 22.36 |

-continued

| | C (%) | H (%) | N (%) |
|---|---|---|---|
| Found: | 65.94; | 6.21; | 22.30 |

$^1$H-NMR (CDCl$_3$)δ: 0.87 (3H, t), 1.13–1.70 (4H, m), 2.50 (2H, t), 3.00 (3H, brs), 3.27 (3H, brs), 5.13 (2H, s), 6.30 (1H, s), 6.87 (2H, d), 6.97 (2H, d), 7.30–7.60 (3H, m), 7.70–7.80 (1H, m)

WORKING EXAMPLE 11

5-Butyl-N-methyl-1-[[2'-(1H-tetrazol-5-yl)biphenyl-4-yl]methyl]pyrazole-3-carboxamide m.p. : 196°–197° C.
yield: 35%
Elemental analysis for C$_{23}$H$_{25}$N$_5$O.7/10H$_2$O

| | C (%) | H (%) | N (%) |
|---|---|---|---|
| Calc.: | 64.64; | 6.02; | 22.71 |
| Found: | 64.53; | 6.22; | 22.90 |

$^1$H-NMR (CDCl$_3$)δ: 0.87 (3H, t), 1.07–1.67 (4H, m), 2.47 (2H, t), 2.80 (3H, d), 5.23 (2H, s), 6.50 (1H, s), 6.83–7.13 (5H, m), 7.27–7.70 (3H, m), 7.80–8.00 (1H, m)

WORKING EXAMPLE 12

5-Butyl-N-ethyl-1-[[2'-(1H-tetrazol-5-yl)biphenyl-4-yl]methyl]pyrazole-3-carboxamide m.p. : 200°–201° C.
yield: 62%
Elemental analysis for C$_{24}$H$_{27}$N$_7$O.1/5H$_2$O

| | C (%) | H (%) | N (%) |
|---|---|---|---|
| Calc.: | 66.55; | 6.38; | 22.64 |
| Found: | 66.65; | 6.22; | 22.84 |

$^1$H-NMR (CDCl$_3$)δ: 0.89 (3H, t), 1.20 (3H, t), 1.35 (2H, m), 1.46–1.75 (2H, m), 2.51 (2H, t), 3.31–3.45 (2H, m), 5.28 (2H, s), 6.54 (1H, s), 6.88 (1H, t), 7.02 (2H, d), 7.16 (2H, d), 7.39–7.43 (1H, m), 7.50–7.64 (2H, m), 8.05 (1H, q)

WORKING EXAMPLE 13

5-Butyl-N-propyl-1-[[2'-(1H-tetrazol-5-yl)biphenyl-4-yl]methyl]pyrazole-3-carboxamide m.p. : 164°–165° C.
yield: 50%
Elemental analysis for C$_{25}$H$_{29}$N$_7$O

| | C (%) | H (%) | N (%) |
|---|---|---|---|
| Calc.: | 67.70; | 6.59; | 22.11 |
| Found: | 67.88; | 6.56; | 21.94 |

$^1$H-NMR CDCl$_3$δ: 0.88 (3H, t), 0.94 (3H, t), 1.33 (2H, m), 1.46–1.67 (4H, m), 2.48 (2H, t), 3.28 (2H, q), 5.27 (2H, s), 6.50 (1H, s), 6.94 (1H, t), 6.97 (2H, d), 7.12 (2H, d), 7.40 (1H, q), 7.4–7.63 (2H, m), 7.99 (1H, d)

WORKING EXAMPLE 14

5-Butyl-1-[[2'-(1H-tetrazol-5-yl)biphenyl-4-yl]methyl]-pyrazole-3-carboxamide m.p. : 205°–206° C.
yield: 26%

Elemental analysis for C$_{22}$H$_{23}$N$_7$O.4/5H$_2$O

| | C (%) | H (%) | N (%) |
|---|---|---|---|
| Calc.: | 63.54; | 5.96; | 23.58 |
| Found: | 63.34; | 5.59; | 23.29 |

$^1$H-NMR (CDCl$_3$)δ: 0.90 (3H, t), 1.13–1.73 (4H, m), 2.52 (2H, t), 5.30 (2H, s), 6.63 (1H, s), 7.03 (2H, d), 7.13 (2H, d), 7.37–7.80 (4H, m)

WORKING EXAMPLE 15

5-Butyl-N-(2-methoxyethyl)-1-[[2'-(1H-tetrazol-5-yl)biphenyl-4-yl]methyl]pyrazole-3-carboxamide m.p. : powder
yield: 79%
Elemental analysis for C$_{25}$H$_{29}$N$_7$O$_2$.2/5H$_2$O

| | C (%) | H (%) | N (%) |
|---|---|---|---|
| Calc.: | 64.33; | 6.44; | 21.01 |
| Found: | 64.49; | 6.29; | 20.97 |

$^1$H-NMR (CDCl$_3$)δ: 0.87 (3H, t), 1.13–1.80 (4H, m), 2.50 (2H, t), 3.33 (3H, s), 3.43–3.57 (4H, m), 5.23 (2H, s), 6.50 (1H, s), 6.93 (2H, d), 7.07 (2H, d), 7.33–7.67 (3H, m), 7.83–8.07 (1H, m)

WORKING EXAMPLE 16

5-Butyl-N-isopropyl-1-[[2'-(1H-tetrazol-5-yl)biphenyl-4-yl]methyl]pyrazole-3-carboxamide m.p. : powder
yield: 77%
Elemental analysis for C$_{25}$H$_{28}$N$_4$O$_2$.2/5H$_2$O

| | C (%) | H (%) | N (%) |
|---|---|---|---|
| Calc.: | 66.62; | 6.66; | 21.75 |
| Found: | 66.73; | 6.56; | 21.81 |

$^1$H-NMR (CDCl$_3$)δ: 0.87 (3H, t), 1.13–1.73 (10H, m), 2.43 (2H, t), 4.07 (1H, m), 5.23 (2H, s), 6.43 (1H, s), 6.73 (1H, d), 6.90 (2H, d), 7.03 (2H, d), 7.30–7.60 (3H, m), 7.83–7.97 (1H, m)

WORKING EXAMPLE 17

Isopropyl 5-butyl-1-[[2'-(1H-tetrazol-5-yl)biphenyl-4-yl]methyl]-pyrazole-3-carboxylate m.p. : powder
yield: 56%
Elemental analysis for C$_{25}$H$_{28}$N$_6$O$_2$.1/5H$_2$O

| | C (%) | H (%) | N (%) |
|---|---|---|---|
| Calc.: | 67.00; | 6.39; | 18.75 |
| Found: | 67.31; | 6.51; | 18.50 |

$^1$H-NMR (CDCl$_3$)δ: 0.87 (3H, t,), 1.17–1.73 (4H, m), 2.53 (2H, t), 3.77 (3H, s), 5.20 (2H, s), 6.60 (1H, s), 6.90 (2H, d), 7.03 (2H, d), 7.27–7.63 (3H, m), 7.77–7.93 (1H, m)

WORKING EXAMPLE 18

Ethyl 5-pentyl-1-[[2'-(1H-tetrazol-5-yl)biphenyl-4-yl]methyl]-pyrazole-3-carboxylate m.p. : 55°-57° C.
yield: 43%
Elemental analysis for $C_{25}H_{28}N_6O_2 \cdot \frac{3}{4}H_2O$

|  | C (%) | H (%) | N (%) |
|---|---|---|---|
| Calc.: | 65.56; | 6.27; | 18.35 |
| Found: | 65.65; | 6.28; | 17.98 |

$^1$H-NMR CDCl$_3$)δ: 0.88 (3H, t), 1.2–1.4 (7H, m), 1.55–1.71 (2H, m), 2.57 (2H, t), 4.32 (2H, q), 5.24 (2H, s), 6.63 (1H, s), 6.98 (2H, d), 7.09 (2H, d), 7.38 (1H, q), 7.44–7.61 (2H, m), 7.96 (1H, q)

WORKING EXAMPLE 19

Ethyl 5-propyl-1-[[2'-(1H-tetrazol-5-yl)biphenyl-4-yl]methyl]-pyrazole-3-carboxylate m.p. : syrup
yield: 18%
Elemental analysis for $C_{23}H_{24}O_2 \cdot 0.7H_2O$

|  | C (%) | H (%) | N (%) |
|---|---|---|---|
| Calc.: | 64.38; | 5.97; | 19.59 |
| Found: | 64.59; | 5.91; | 19.34 |

$^1$H-NMR (CDCl$_3$)δ: 0.92 (3H, t), 1.35 (3H, t), 1.62 (2H, m), 4.30 (2H, q), 5.66 (2H, s), 6.69 (1H, s), 7.13 (4H, brs), 7.39 (1H, q), 7.48–7.62 (2H, m), 8.07 (1H, m)

WORKING EXAMPLE 20

2,2,2-Trifluoroethyl 5-butyl-1-[[2'-(1H-tetrazol-5-yl)biphenyl-4-yl]methyl]-pyrazole-3-carboxylate N-Chlorosuccinimide (400 mg) was added to a stirred solution of 5-butyl-1-[[2'-(1H-tetrazol-5-yl)biphenyl-4-yl]methyl]pyrazole-3-carboxylic acid (682 mg), triethylamine (1.2 g), 2,2,2-trifluoroethanol (248 mg) and triphenylphosphine (891 mg) in dichloromethane (30 ml) by cooling with an ice-bath. After stirring for 15 minutes, triphenylphosphine (262 mg) and N-chlorosuccinimide (133 mg) were added and the mixture was stirred for 30 minutes. After addition of 2N-hydrochloric acid (15 ml) and stirring at room temperature for 30 minutes, the mixture was allowed to separate into layers. The organic layer was washed with water, dried, and concentrated to dryness to give a syrup, which was then purified by column chromatography on silica gel, to give a yellow syrup (460 mg, 58%).

Elemental analysis for $C_{24}H_{24}N_6O_2F_3$

|  | C (%) | H (%) | N (%) |
|---|---|---|---|
| Calc.: | 59.38; | 4.98; | 17.31 |
| Found: | 59.64; | 4.93; | 17.01 |

$^1$H-NMR (CDCl$_3$)δ: 0.90 (3H, t), 1.07–1.77 (4H, m), 2.57 (2H, t), 4.63 (2H, q), 5.30 (2H, s), 6.67 (1H, s), 6.93–7.67 (7H, m), 7.87–8.00 (1H, m)

IR (Nujol)cm$^{-1}$: 2725, 1750, 1445, 1280, 1200, 1165, 1115, 985, 755

In the same way as in the Working Example 20, the following compounds were synthesized.

WORKING EXAMPLE 21

1,1,1,3,3,3-Hexafluoroisopropyl 5-butyl-1-[[2'-(1H-tetrazol-5-yl)biphenyl-4-yl]methyl]-pyrazole-3carboxylate m.p. : syrup
yield: 27%
Elemental analysis for $C_{25}H_{22}N_6O_2F_6$

|  | C (%) | H (%) | N (%) |
|---|---|---|---|
| Calc.: | 54.35; | 4.01; | 15.21 |
| Found: | 54.67; | 4.06; | 14.85 |

$^1$H-NMR CDCl$_3$)δ: 0.90 (3H, t), 1.07–1.80 (4H, m), 2.60 (2H, t), 5.33 (2H, s), 5.97 (1H, m), 6.70 (1H, s), 7.00–7.70 (7H, m), 7.90–8.07 (1H, m)

IR (Nujol)cm : 1765, 1390, 1290, 1230, 1200, 1170, 1110

WORKING EXAMPLE 22

Methyl 5-butyl-1-[[2'-(1H-tetrazol-5-yl)biphenyl-4-yl]methyl]-pyrazole-3-carboxylate m.p. : powder
yield: 65%
Elemental analysis for $C_{23}H_{24}N_6O_2 \cdot \frac{1}{2}H_2O$

|  | C (%) | H (%) | N (%) |
|---|---|---|---|
| Calc.: | 64.93; | 5.92; | 19.75 |
| Found: | 65.04; | 5.93; | 19.42 |

$^1$H-NMR (CDCl$_3$)δ:0.87 (3H, t), 1.17–1.73 (4H, m), 2.53 (2H, t), 3.77 (3H, s), 5.20 (2H, s), 6.60 (1H, s), 6.90 (2H, d), 7.03 (2H, d), 7.27–7.63 (3H, m), 7.77–7.93 (1H, m)

IR (CHCl$_3$)cm$^{-1}$: 3000, 2965, 2930, 2875, 2745, 1730, 1475, 1445, 1390, 1225, 1010, 910, 820

WORKING EXAMPLE 23

Ethyl 5-butyl-1-[[2'-(1H-tetrazol-5-yl)biphenyl-4-yl]methyl]-pyrazole-3-carboxylate The same product as that in the Working Example 1 was obtained in a 68% yield.

WORKING EXAMPLE 24

Isopropyl 5-butyl-1-[[2'-(1H-tetrazol-5-yl)biphenyl-4-yl]methyl]-pyrazole-3-carboxamide The same product as that in the Working Example 17 was obtained in 65% yield.

WORKING EXAMPLE 25

5-Butyl-N,N-tetramethylene-1-[[2'-(1H-tetrazol-5-yl)biphenyl-4-yl]methyl]pyrazole-3-carboxamide To a stirred solution of 5-butyl-1-[[2'-(1H-tetrazol-5-yl)biphenyl-4-yl]methyl]pyrazole-3-carboxylic acid (416 mg), triethylamine (500 mg), pyrrolidine (200 mg) and triphenylphosphine (786 mg) in dichloromethane (20 ml) was added N-chlorosuccinimide (400 mg) by cooling with an ice-bath. After stirring at the same temperature for 30 minutes, 0.2 N-HCl (50 ml) was added, followed by extraction with ether. The organic layer was washed with water, and extracted with 0.1 N-NaOH. The aqueous layer was washed with ether, and made acidic with 0.2N-HCl acid, followed by extraction with chloroform. The syrup obtained by drying and concentration was purified by column chromatography on silica gel to give the desired compound as a syrup (200 mg, 44%).

Elemental analysis for $C_{26}H_{29}N_7O.3/10H_2O$

|  | C (%) | H (%) | N (%) |
|---|---|---|---|
| Calc.: | 67.75; | 6.47; | 21.27 |
| Found: | 67.84; | 6.36; | 20.98 |

$^1$H-NMR (CDCl$_3$)δ: 0.87 (3H, t), 1.13–1.67 (4H, m), 1.77–2.03 (4H, m), 2.47 (2H, t), 3.50 (2H, t), 3.87 (2H, t), 5.20 (2H, s), 6.40 (1H, s), 6.90 (2H, d), 7.00 (2H, d), 7.30–7.63 (3H, m), 7.80–7.90 (1H, m)

WORKING EXAMPLE 26

5-Butyl-1-[[2'-(1H-tetrazol-5-yl)biphenyl-4-yl]methyl]-pyrazole-3-carboxylic acid 5-Butyl-1-[(2'-cyanobiphenyl-4-yl)methyl]pyrazole-3-carboxylic acid (17.6 g), sodium azide (19.5 g), and ammonium chloride (13.4 g) were stirred in dimethylformamide (DMF) (140 ml) at 110°–120° C. for 5 days. The reaction mixture was poured into water (1.2 l), to which conc. HCl (35 ml) and ethyl acetate (700 ml) were added. The organic layer was washed with 0.1 N-HCl and water, dried, and concentrated under reduced pressure. To the residue was added ether, and the resultant crude crystals were recrystallized from ethyl acetate-ether to give colorless crystals (16.3 g, 83%).

m.p. 164°–166° C.
Elemental analysis for $C_{22}H_{21}N_6O_2.3/10H_2O$

|  | C (%) | H (%) | N (%) |
|---|---|---|---|
| Calc.: | 64.95; | 5.35; | 20.66 |
| Found: | 64.83; | 5.50; | 20.96 |

$^1$H-NMR (CDCl$_3$-CD$_3$OD)δ: 0.87 (3H, t), 1.13–1.77 (4H, m), 2.57 (3H, t), 5.27 (2H, s), 6.63 (1H, s), 6.97 (2H, d), 7.07 (2H, d), 7.37–7.60 (3H, m), 7.77–7.93 (2H, m)
IR (Nujol)cm.: 2760, 2610, 1695, 1505, 1450, 1265, 760

The following compounds (Working Examples 27–29) were prepared by a method analogous to that of working Example 25.

WORKING EXAMPLE 27

5-Butyl-3-(N-morpholinocarbonyl)-1-[[2'-(1H-tetrazol-5-yl)biphenyl-4-yl]methyl]pyrazole m.p. : colorless powder
Yield: 91%
Elemental analysis for $C_{26}H_{29}N_7O_2.\frac{1}{2}H_2O$

|  | C (%) | H (%) | N (%) |
|---|---|---|---|
| Calc.: | 64.98; | 6.29; | 20.40 |
| Found: | 64.98; | 6.09; | 20.38 |

$^1$H-NMR (90MHz, CDCl$_3$)δ: 0.90 (3H, t), 1.23–1.73 (4H, m), 2.50 (2H, t), 3.70 (8H, brs], 5.20 (2H, s), 6.37 (1H, s), 6.93 (2H, d), 7.03 (2H, d), 7.30–7.67 (3H, m), 7.83–7.93 (1H, m)
IR (Nujol)cm$^{-1}$: 2715, 1590, 1480, 1235, 1110, 990, 760

WORKING EXAMPLE 28

5-Butyl-N-(3-ethoxycarbonylphenyl)-1-[[2'-(1H-tetrazol-5-yl)biphenyl-4-yl]methyl]pyrazole-3carboxamide m.p. : colorless powder
Yield: 76%
Elemental analysis for $C_{31}H_{31}N_7O_3.\frac{1}{2}H_2O$

|  | C (%) | H (%) | N (%) |
|---|---|---|---|
| Calc.: | 66.65; | 5.77; | 17.55 |
| Found: | 66.66; | 5.75; | 17.32 |

$^1$H-NMR (90MHz, CDCl$_3$)δ: 0.87 (3H, t), 1.20–1.73 (7H, m), 2.50 (2H, t), 4.33 (2H, q), 5.23 (2H, s), 6.63 (1H, s), 6.93 (2H, d), 7.03 (2H, d), 7.27–8.17 (12H, m), 8.90 (1H, brs)
IR (Nujol)cm$^{-1}$: 3325, 1725, 1675, 1545, 1300, 1285, 1225, 1200

WORKING EXAMPLE 29

5-Butyl-N-(α-ethoxycarbonylbenzyl)-1-[[2'-(1H-tetrazol-5-yl)biphenyl-4-yl]methyl]pyrazole-3carboxamide m.p. : colorless powder Yield: 41%
Elemental analysis for $C_{32}H_{33}N_7O_3.\frac{1}{2}H_2O$

|  | C (%) | H (%) | N (%) |
|---|---|---|---|
| Calc.: | 67.12; | 5.98; | 17.12 |
| Found: | 67.32; | 5.92; | 17.04 |

$^1$H-NMR (90MHz, CDCl$_3$)δ: 0.87 (3H, t), 1.10–1.73 (7H, m), 2.50 (2H, t), 4.00–4.37 (2H, m), 5.20 (2H, s), 5.70 (1H, d), 6.53 (1H, s), 6.93 (2H, d), 7.07 (2H, d), 7.27–7.60 (13H, m), 7.77 (1H, d), 7.83–8.03 (1H, m)
IR (Nujol)cm$^{-1}$: 3390, 1740, 1650, 1525

WORKING EXAMPLE 30

5-Butyl-N-(4-chlorophenyl)-1-[[2'-(1H-tetrazol-5-yl)biphenyl-4-yl]methyl]pyrazole-3-carboxamide A solution of 5-butyl-1-[[2'-(1H-tetrazol-5-yl)-biphenyl-4-yl]methyl]pyrazole-3-carboxylic acid (0.8 g) and diethyl phosphorocyanidate (90% purity, 0.76 g) in DMF (6 ml) was allowed to stir at 0°–5° C. for 1 hour. 4-Chloroaniline (0.25 g) and triethylamine (0.62 g) were added to the solution and the mixture was stirred at room temperature for 3 hours. The reaction solution was made acidic by addition of 1N-HCl and extracted with ethyl acetate. The organic layer was dried and evaporated to dryness to give a syrup. The syrup was purified by column chromatography on silica gel to give colorless powder (0.38 g, 38%);
m.p. : 106°–108° C.
Elemental analysis for $C_{28}H_{26}ClN_7O.0.3H_2O$

|  | C (%) | H (%) | N (%) |
|---|---|---|---|
| Calc.: | 65.00; | 5.18; | 18.95 |

|  | C (%) | H (%) | N (%) |
|---|---|---|---|
| Found: | 65.07; | 5.34; | 18.46 |

$^1$H-NMR (200MHz, CDCl$_3$)δ: 0.89 (3H, t), 1.26–1.44 (2H, m), 1.50–1.65 (2H, m), 2.51 (2H, t), 5.27 (2H, s), 6.66 (1H, s), 7.00 (2H, d), 7.12 (2H, d), 7.25–7.29 (2H, m), 7.36–7.40 (1H, m), 7.47–7.62 (4H, m), 8.00 (1H, dd), 8.77 (1H, s)

IR (KBr)cm$^{-1}$: 1675, 1645, 1590, 1535, 1490, 1395 1300, 820, 755

The following compounds (Working Examples 31–35 and 37) were prepared by a method analogous to that of Example 30.

WORKING EXAMPLE 31

5-Butyl-3-(4-diphenylmethylpiperazinylcarbonyl)-1-[[2'-(1H-tetrazol-5-yl)biphenyl-4-yl]methyl]pyrazole m.p. : 120°–121° C.
Yield: 64%
Elemental analysis for C$_{39}$H$_{40}$N$_8$O.½H$_2$O

|  | C (%) | H (%) | N (%) |
|---|---|---|---|
| Calc.: | 72.53; | 6.40; | 17.35 |
| Found: | 72.36; | 6.41; | 17.08 |

$^1$H-NMR (200MHz, CDCl$_3$)δ: 0.88 (3H, t), 1.22–1.42 (2H, m), 1.48–1.61 (2H, m), 2.33–2.51 (6H, m), 3.72 (2H, m), 3.92 (2H, m), 4.25 (1H, s), 5.13 (2H, s), 6.30 (1H, s), 6.85 (2H, d), 6.95 (2H, d), 7.14–7.34 (5H, m), 7.40–7.56 (8H, m), 7.81 (1H, dd)

IR (KBr)cm$^{-1}$: 1615, 1595, 1495, 1445, 1235, 995, 760, 700

WORKING EXAMPLE 32

5-Butyl-3-(4-diphenylmethylpiperidinocarbonyl)-1-[[2'-(1H-tetrazol-5-yl)biphenyl-4-yl]methyl]pyrazole m.p. : 128°–130° C.
Yield: 38%
Elemental analysis for C$_{40}$H$_{41}$N$_7$O.½H$_2$O

|  | C (%) | H (%) | N (%) |
|---|---|---|---|
| Calc.: | 74.51; | 6.57; | 15.21 |
| Found: | 74.53; | 6.69; | 14.88 |

$^1$H-NMR (200MHz, CDCl$_3$)δ: 0.87 (3H, t), 1.06–1.66 (7H, m), 2.22–2.50 (3H, m), 2.67 (1H, t), 3.03 (1H, t), 3.49 (1H, d), 4.52 (2H, t), 5.10 (2H, s), 6.24 (1H, s), 6.82 (2H, d), 6.91 (2H, d), 7.17–7.34 (1H, m), 7.38–7.55 (2H, m), 7.77 (1H, dd)

IR (KBr)cm$^{-1}$: 1590, 1495, 1445, 1370, 1270, 1250, 1200, 970, 755, 700

WORKING EXAMPLE 33

5-Butyl-N-(4-methoxyphenyl)-1-[[2'-(1H-tetrazol-5-yl)biphenyl-4-yl]methyl]pyrazole-3-carboxamide m.p. : 97°–98° C.
Yield: 46%
Elemental analysis for C$_{29}$H$_{29}$N$_7$O$_2$.½H$_2$O

|  | C (%) | H (%) | N (%) |
|---|---|---|---|
| Calc.: | 67.42; | 5.85; | 18.98 |
| Found: | 67.67; | 5.69; | 18.71 |

$^1$H-NMR (200MHz, CDCl$_3$)δ: 0.86 (3H, t), 1.22–1.39 (2H, m), 1.43–1.58 (2H, m), 2.46 (2H, t), 3.77 (3H, s), 5.18 (2H, s), 6.58 (1H, s), 6.81–6.90 (4H, m), 7.01 (2H, d), 7.34–7.59 (5H, m), 7.83 (1H, d), 8.76 (1H, s),

IR (KBr)cm$^{-1}$: 3400, 1675, 1640, 1600, 1530, 1515, 1465, 1440, 1245, 1230, 825, 760

WORKING EXAMPLE 34

5-Butyl-N-(4-methylphenyl)-1-[[2'-(1H-tetrazol-5-yl)biphenyl-4-yl]methyl]pyrazole-3-carboxamide m.p. : 97°–99° C.
Yield: 60%
Elemental analysis for C$_{29}$H$_{29}$N$_7$O.0.7H$_2$O

|  | C (%) | H (%) | N (%) |
|---|---|---|---|
| Calc.: | 69.08; | 6.08; | 19.45 |
| Found: | 69.14; | 5.87; | 19.15 |

$^1$H-NMR (200MHz, CDCl$_3$)δ: 0.87 (3H, t), 1.23–1.41 (2H, m), 1.46–1.61 (2H, m), 2.31 (3H, s), 2.48 (2H, t), 5.22 (2H, s), 6.60 (1H, s), 6.93 (2H, d), 7.04–7.13 (4H, m), 7.37 (1H, dd), 7.46–7.59 (4H, m), 7.90 (1H, d), 8.71 (1H, s),

IR (KBr)cm 3400, 1645, 1600, 1530, 1480, 1450, 400, 1380, 1310, 1295, 1240, 1200, 1100, 815, 750

WORKING EXAMPLE 35

2-(4-Diphenylmethylpiperazinyl)ethyl 5-butyl-1-[[2'-(1H-tetrazol-5-yl)biphenyl-4-yl]methyl]-pyrazole-3-carboxylate m.p. : 200°–201° C. (dec.)
Yield: 30%
Elemental analysis for C$_{41}$H$_{44}$N$_8$O$_4$

|  | C (%) | H (%) | N (%) |
|---|---|---|---|
| Calc.: | 72.33; | 6.51; | 16.46 |
| Found: | 72.15; | 6.51; | 16.28 |

$^1$H-NMR (200MHz, CDCl$_3$)δ: 0.99 (3H, t), 1.38–1.56 (2H, m), 1.65–1.81 (2H, m), 2.16 (4H, m), 2.46 (4H, m), 2.72–2.79 (4H, m), 3.72 (1H, s), 4.32–4.37 (2H, m), 5.19 (2H, s), 6.71 (1H, s), 7.1–7.3 (14H, m), 7.52–7.69 (3H, m), 8.19–8.23 (1H, m)

IR (KBr)cm 1730, 1445, 1210, 760, 740, 705

WORKING EXAMPLE 36

5-Butyl-N-(α-carboxybenzyl)-1-[[2'-(1H-tetrazol-5-yl)biphenyl-4-yl]methyl]pyrazole-3-carboxamide A solution of 5-butyl-N-(α-ethoxycarbonylbenzyl)-1-[[2'-cyanobiphenyl-4-yl)methyl]pyrazole-3-carboxamide (0.45 g) in methanol (10 ml) containing 2N-NaOH (1.5 was allowed to stand at room temperature for 1.5 hours. Water (20 ml) was added to the reaction solution and methanol was removed by evaporation in vacuo. The resulting solution was made acidic by addition of 2N-HCl to give a syrup. The syrup was extracted with ethyl acetate and the extract was dried and evaporated to dryness to give a syrup. The syrup was purified by column chromatography on silica gel to give a colorless powdery product (0.3 g, 70%).

Elemental analysis for $C_{30}H_{29}N_7O_3 \cdot 1/5H_2O$

|  | C (%) | H (%) | N (%) |
|---|---|---|---|
| Calc.: | 66.83; | 5.50; | 18.18 |
| Found: | 66.65; | 5.81; | 18.42 |

$^1$H-NMR (90MHz, DMSO-$d_6$)δ: 0.87 (3H, t), 1.13–1.73 (4H, m), 2.53 (2H, t), 5.23 (2H, s), 5.47 (1H, d), 6.50 (1H, s), 6.77 (2H, d), 6.97–7.67 (11H, m), 8.27 (1H, d)

IR (Nujol) cm 3400, 1630, 1555, 1530, 1425 1410, 1380, 760

WORKING EXAMPLE 37

5-Butyl-N-(3-carboxyphenyl)-1-[[2'-(1H-tetrazol-5-yl)biphenyl-4-yl]methyl]pyrazole-3-carboxamide The compound was obtained by a method analogous to that of Example 35.

m.p. : colorless powder
Yield: 86%
Elemental analysis for $C_{29}H_{27}N_7O_3 \cdot \frac{1}{2}H_2O$

|  | C (%) | H (%) | N (%) |
|---|---|---|---|
| Calc.: | 65.65; | 5.32; | 18.48 |
| Found: | 65.37; | 5.60; | 18.39 |

$^1$H-NMR (90MHz, DMSO-$d_6$)δ: 0.90 (3H, t), 1.13–1.77 (7H, m), 2.60 (2H, t), 5.37 (2H, s), 6.67 (1H, s), 7.10 (4H, s), 7.30–7.80 (10H, m), 8.03 (1H, d), 8.33 (1H, m), 9.40 (1H, brs).

IR (Nujol) cm$^{-1}$: 3060, 2630, 1730, 1690, 1650, 1590, 1550, 750

PREPARATION EXAMPLE

When the compound (I) of the present invention is used as a therapeutic for cardiovascular diseases including hypertension, heart disease, and cerebral stroke, the compound can be used according, for example, to the following recipes.

1. Capsules

| (1) isopropyl 5-butyl-1-[[2'-(1H-tetrazol-5-yl)biphenyl-4-yl]methyl]pyrazole-3-carboxylate | 20 mg |
|---|---|
| (2) lactose | 90 mg |
| (3) fine crystalline cellulose | 70 mg |
| (4) magnesium stearate | 10 mg |
| one capsule | 190 mg |

(1), (2), (3), and a half of (4) are mixed and granulated. To the granules is added the remainder of (4), and the whole is included in gelatin capsules.

2. Tables

| (1) ethyl 5-butyl-1-[[2'-(1H-tetrazol-5-yl)biphenyl-4-yl]methyl]pyrazole-3-carboxylate | 10 mg |
|---|---|
| (2) lactose | 35 mg |
| (3) Corn starch | 150 mg |
| (4) fine crystalline cellulose | 30 mg |
| (5) magnesium stearate | 5 mg |
| one tablet | 230 mg |

(1), (2), (3), two thirds of (4), and a half of (5) are mixed and granulated. To the granules are added the remainders of (4) and (5), followed by press-shaping into tablets.

3. Injections

| (1) 5-butyl-N-isopropyl-1-[[2'-(1H-tetrazol-5-yl)biphenyl-4-yl]methyl]pyrazole-3-carboxamide | 10 mg |
|---|---|
| (2) inositol | 100 mg |
| (3) benzyl alcohol | 20 mg |
| one ampul | 130 mg |

(1), (2), and (3) are dissolved in the distilled water for injection to make 2 ml, and the resultant solution is included in ampuls. The whole process is conducted under sterile conditions.

EXPERIMENTAL EXAMPLE 1

Inhibition of binding of angiotensin II to angiotensin receptors

Method

An experiment of inhibition of angiotensin II (A (II) receptor binding was conducted according to the modified Douglas et al's method [Endocrinology, 102, 685–695 (1978)]. An A II receptor membrane fraction was prepared from bovine adrenal cortex.

the compound of the present invention ($10^{-6}$–$10^{-5}$M) and $^{125}$I-angiotensin II ($^{125}$I-A II) (1.85 kBq/50 μl) were added to the receptor membrane fraction and incubated at room temperature for 1 hour. Bound and free $^{125}$I-A II's were separated through a filter (Whatman GF/B filter), and the radioactivity of $^{125}$I-A II bound to the receptor was measured.

Result

The results related to the compounds of the present invention are shown in Table 1.

TABLE 1

| Working Example No. | Inhibition of angiotensin $1 \times 10^{-6}$ (M) | II receptor binding (%) $1 \times 10^{-5}$ (M) |
|---|---|---|
| 1 | 75 | 92 |
| 2 | 80 | 95 |
| 3 | 81 | 94 |
| 5 | 93 | 98 |
| 6 | 83 | 95 |
| 7 | 91 | 97 |
| 8 | 86 | 95 |
| 9 | 73 | 96 |
| 12 | 85 | 97 |
| 13 | 85 | 99 |
| 14 | 75 | 93 |
| 15 | 88 | 95 |
| 16 | 91 | 95 |
| 17 | 91 | 98 |
| 18 | 54 | 88 |
| 19 | 62 | 90 |
| 20 | 66 | 94 |
| 22 | 61 | 90 |
| 25 | 77 | 96 |
| 27 | 92 | 97 |
| 31 | 38 | 89 |
| 32 | 32 | 88 |

What is claimed is:

1. A compound which is 5-butyl-N-(2-methoxyethyl)-1-[[2'-(1H)-tetrazol-5-yl)biphenyl-4-yl]methyl]pyrazole-3-carboxamide.

* * * * *